(12) United States Patent
Ehrmann et al.

(10) Patent No.: US 9,936,867 B2
(45) Date of Patent: *Apr. 10, 2018

(54) SYSTEM AND METHOD FOR CHARACTERISING EYE-RELATED SYSTEMS

(71) Applicant: Brien Holden Vision Institute, Sydney, New South Wales (AU)

(72) Inventors: Klaus Ehrmann, Queenscliff (AU); Darrin Mark Falk, Stanmore (AU); Cathleen Fedtke, Sydney (AU)

(73) Assignee: Brien Holden Vision Institute, Sydney, New South Wales (AU)

( * ) Notice: Subject to any disclaimer, the term of this patent is extended or adjusted under 35 U.S.C. 154(b) by 0 days.

This patent is subject to a terminal disclaimer.

(21) Appl. No.: 15/240,665

(22) Filed: Aug. 18, 2016

(65) Prior Publication Data
US 2017/0095149 A1    Apr. 6, 2017

Related U.S. Application Data

(63) Continuation of application No. 14/131,381, filed as application No. PCT/AU2012/000816 on Jul. 6, 2012, now Pat. No. 9,445,717.

(30) Foreign Application Priority Data

Jul. 8, 2011    (AU) ................................ 2011902736

(51) Int. Cl.
*A61B 3/10*    (2006.01)
*A61B 3/14*    (2006.01)
(Continued)

(52) U.S. Cl.
CPC .......... *A61B 3/1015* (2013.01); *A61B 3/0008* (2013.01); *A61B 3/0025* (2013.01);
(Continued)

(58) Field of Classification Search
USPC .................................................. 351/200–246
See application file for complete search history.

(56) References Cited

U.S. PATENT DOCUMENTS

| | | | |
|---|---|---|---|
| 5,024,519 | A | 6/1991 | Howard |
| 5,532,771 | A | 7/1996 | Johnson et al. |

(Continued)

FOREIGN PATENT DOCUMENTS

| | | |
|---|---|---|
| WO | WO 2005/102418 | 11/2005 |
| WO | WO 2008/116270 | 10/2008 |

OTHER PUBLICATIONS

Atchison, "Comparison of Peripheral Refractions Determined by Different Instruments", Optometry and Vision Science, vol. 80, No. 9, pp. 655-660, 2003.

(Continued)

*Primary Examiner* — Mohammed Hasan
(74) *Attorney, Agent, or Firm* — Jones Day

(57) ABSTRACT

Described herein is a light directing assembly for use in an object analysis system. The light directing assembly includes a plurality of optical relay assemblies. Each optical relay assembly includes at least one optical element configured to relay an interrogation beam from a light transmission system to an object and relay a return beam from the object to the light transmission system, the return beam being generated by reflection or back scattering of the interrogation beam by the object. Each optical relay assembly defines an interrogation angle at which the interrogation beam relayed by the optical relay assembly reaches the object, and an optical path length being the distance from the light transmission system to the object traveled by an interrogation beam via the optical relay assembly. The plurality of optical relay assemblies are further configured such that the optical path length for a given optical relay assembly has a (Continued)

predefined relationship with the optical path lengths of the other optical relay assemblies.

29 Claims, 11 Drawing Sheets

(51) Int. Cl.
*A61B 3/00* (2006.01)
*G02B 26/10* (2006.01)
*A61B 3/103* (2006.01)
*G02B 13/00* (2006.01)
*G02B 3/00* (2006.01)

(52) U.S. Cl.
CPC ............... *A61B 3/10* (2013.01); *A61B 3/103* (2013.01); *A61B 3/1005* (2013.01); *A61B 3/14* (2013.01); *G02B 13/0095* (2013.01); *G02B 26/101* (2013.01); *G02B 26/105* (2013.01); *G02B 3/0006* (2013.01)

(56) References Cited

U.S. PATENT DOCUMENTS

| | | | |
|---|---|---|---|
| 5,625,428 | A | 4/1997 | Isogai |
| 6,229,562 | B1 | 5/2001 | Kremen |
| 6,409,345 | B1 | 6/2002 | Molebny et al. |
| 6,439,720 | B1 | 8/2002 | Graves et al. |
| 6,460,997 | B1 * | 10/2002 | Frey ................. A61B 3/1015 351/211 |
| 6,634,750 | B2 | 10/2003 | Neal et al. |
| 7,909,465 | B2 | 3/2011 | Ho et al. |
| 9,445,717 | B2 * | 9/2016 | Ehrmann ................. A61B 3/14 |
| 2005/0134796 | A1 | 6/2005 | Zelvin |
| 2005/0163455 | A1 | 7/2005 | Polland |
| 2005/0203422 | A1 | 9/2005 | Wei |
| 2009/0194589 | A1 * | 8/2009 | Moon ....................... G06K 7/12 235/454 |
| 2013/0271729 | A1 * | 10/2013 | Ranchod ................ A61B 3/125 351/206 |

OTHER PUBLICATIONS

Atchison, "Recent advances in measurement of monochromatic aberrations of human eyes", Clinical and Experimental Optometry, vol. 88, pp. 5-27, 2005.
Artal et al., "Refraction, Aliasing, and the Absence of Motion Reversals in Peripheral Vision", Vision Research, vol. 35, No. 7, pp. 939-937, 1995.
Gustafsson et al, "Peripheral astigmatism in emmetropic eyes", Opthal. Physiol. Opt., vol. 21, No. 5, ppp. 393-400, 2001.
Gwiazda et al., "Comparison of Spherical Equivalent Refraction and Astigmatism Measured with Three Different Models of Autorefractors", Optometry and Vision Science, vol. 81, No. 1, pp. 56-61, 2004.
Schmid "Axial and peripheral eye length measured with optical low coherence reflectometry", Journal of Biomedical Optics, vol. 8, No. 4, pp. 655-662, 2003.
Webb et al., "Measurement of ocular local wavefront distortion with a spatially resolved refractometer" Applied Options, vol. 31, No. 19, pp. 3678-3686, 1992.
Schmid, et al., "Measurement of eye length and eye shaper by optical low coherence", International Opthalmology, vol. 23, pp. 317-320, 2001.
International Search Report dated Aug. 13, 2012 for corresponding PCT/AU2012/000816.

* cited by examiner

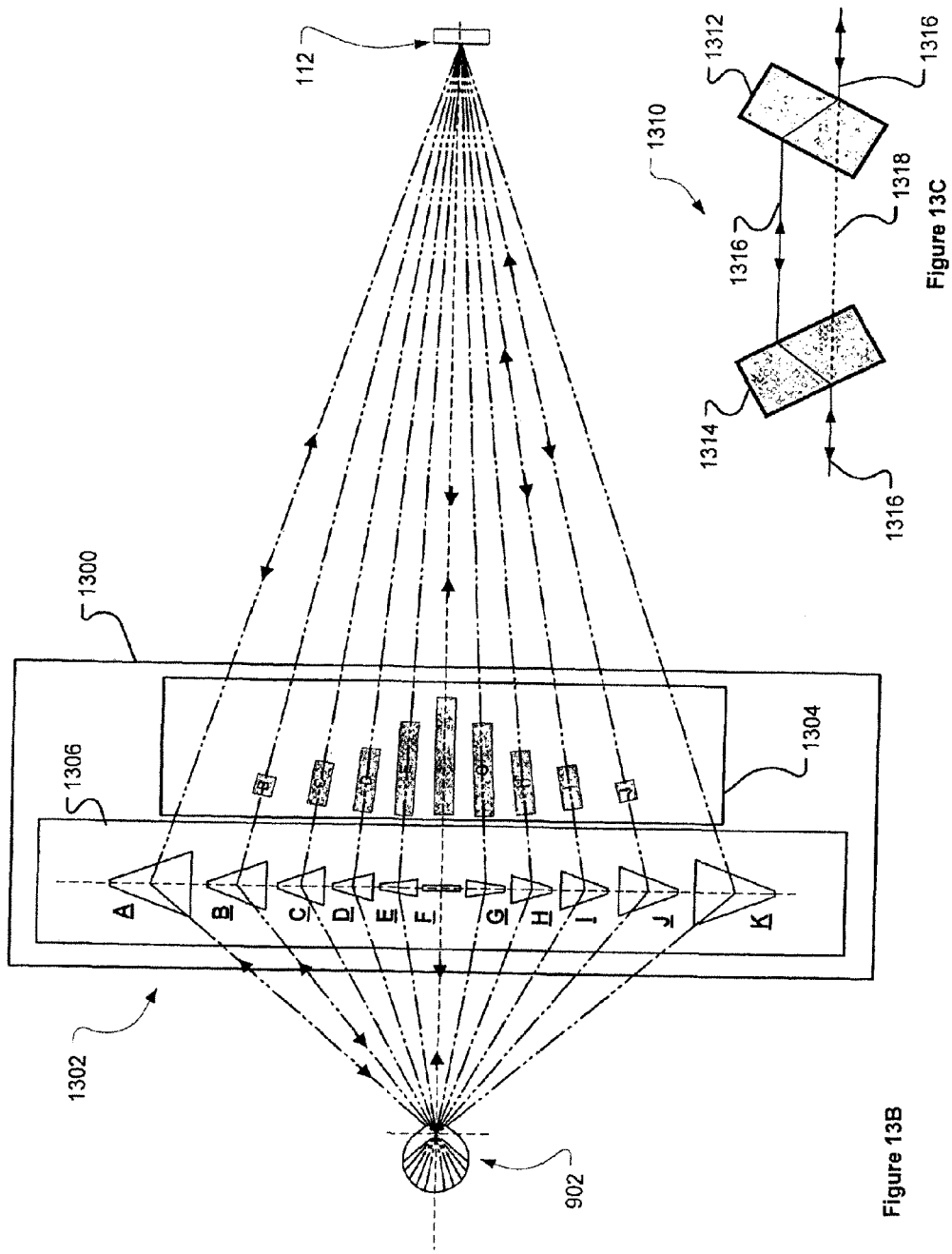

SYSTEM AND METHOD FOR CHARACTERISING EYE-RELATED SYSTEMS

CROSS REFERENCE TO RELATED APPLICATIONS

This application is a continuation of U.S. application Ser. No. 14/131,381, filed Jan. 7, 2014, which is the National Phase application of International Application No. PCT/AU2012/000816, filed Jul. 6, 2012, which designates the United States and was published in English, and which further claims the benefit of priority from Australian Application No. 2011902736, filed Jul. 8, 2011. These applications, in their entirety, are incorporated herein by reference.

FIELD OF THE INVENTION

This invention relates to methods, instruments and system for characterising eye-related systems.

BACKGROUND OF THE INVENTION

Optical characterisation of an eye or eye-related system is an important step in assessing the health of an eye and in diagnosing pathological changes.

Examination of an eye in order to optically characterise the eye may include visual examination of the anterior and posterior eye to assess the health of the eye and diagnose pathological changes. Examination may also include the quantification of optical and anatomical characteristics of the eye. This typically involves refractometry; that is, the determination of the optical power of portion or the entire optical path traveled by an interrogating ray. This may, for example, include mapping—or spatially resolving—refractive power over an area or surface of the eye-related system, which is sometimes referred to as wavefront aberrometry. Determination of the optical and characteristics of the eye may also include the determination of various measurements of the eye-related system, such as the length of the eye-related system (i.e. the distance from the anterior surface of the cornea to the anterior surface of the retina), the profile and/or thickness of the cornea, the pupil size, and the depth of the anterior chamber. Such measurements may be important for certain surgical procedures (e.g. lens replacement or ablative laser treatment).

Several commercial instruments for eye examination are available. These include slit lamp biomicroscopes, anterior segment and retinal OCT instruments, keratometers, autorefractors, fluoro-photometers, ophthalmoscopes and low coherence length and thickness measurement instruments. All of these instruments are designed to make observations or measurements at a single position and at a single, usually central, field angle. If other parts of the eye, or different angles, are to be assessed, either the instrument needs to be rotated and repositioned or the patient has to turn the eyeball or head. This restricts the speed and repeatability with which such measurements/observations can be obtained.

One particular aspect of ocular examinations, where speed and repeatability is critical is the measurement of peripheral refraction. Auto-refractors to measure the lower order aberrations of the eye and Hartmann-Shack aberrometers for higher order aberration measurements are commonly in use to measure central, on-axis refraction and wavefront aberrations. Several methods had been described to modify current instruments to make them suitable for measuring peripheral refraction. These methods usually involve the patient rotating eye or head to fixate at targets which are off-axis to the observation angle. By moving the fixation target, several measurements can be obtained for various peripheral angles and directions. Typically, these measurements are taken sequentially, leading to inaccuracies due to fluctuating fixation, accommodation and alignment and to prolonged measurement time.

Patent publication number WO 2008/116270 A1 titled "Characterising eye-related optical systems" describes an instrument that can measure an eye's refraction at multiple field angles by scanning the measurement beam across the visual field of the eye. The method and instrument described in this application, however, has some limitations as it does not allow for sharp focus to be maintained between observations/measurements at different field angles, and the accuracy of measurements taken from reflected wavefronts and/or images is relatively limited.

It would be desirable to provide methods and/or system capable of characterising-eye related systems by taking measurements and/or making observations from multiple field angles. In addition, it would be desirable to be able to take measurements/make observations with a relatively high degree of accuracy and/or with a relatively short measurement time.

Reference to any prior art in the specification is not, and should not be taken as, an acknowledgment or any form of suggestion that this prior art forms part of the common general knowledge in Australia or any other jurisdiction or that this prior art could reasonably be expected to be ascertained, understood and regarded as relevant by a person skilled in the art.

SUMMARY OF THE INVENTION

In one aspect the present invention provides a light directing assembly for use in an object analysis system, the light directing assembly including: a plurality of optical relay assemblies, each optical relay assembly including at least one optical element configured to: relay an interrogation beam from a light transmission system to an object; and relay a return beam from the object to the light transmission system, the return beam being generated by reflection or back scattering of the interrogation beam by the object, wherein each optical relay assembly defines: an interrogation angle at which the interrogation beam relayed by the optical relay assembly reaches the object, and an optical path length being the distance from the light transmission system to the object traveled by an interrogation beam via the optical relay assembly, and wherein the plurality of optical relay assemblies are further configured such that the optical path length for a given optical relay assembly has a predefined relationship with the optical path lengths of the other optical relay assemblies.

In a second aspect the present invention provides an object analysis system for optically analysing an object, the object analysis system including: a light directing as described in the preceding paragraph; a light source adapted to generate and propagate a source light beam along a source beam path to a light transmission system, the light transmission system optically connected to said source beam path and adapted to generate and direct interrogation beams at each optical relay assembly in the light directing assembly, the light transmission system further adapted to receive return beams from the optical relay assemblies and direct said return beams along said source beam path; a detector for detecting each return beam and generating a detector output data indicative of each detected return beam, and a processing system in communication with said detector, said processor adapted to: receive said detector output data; compare data relating to each detected return beam with data representative of the interrogation beam that generated that return beam; and generate an analysis output indicating aberrations between pairs of return beam data and corresponding interrogation beam data.

As used herein, except where the context requires otherwise, the term "comprise" and variations of the term, such as "comprising", "comprises" and "comprised", are not intended to exclude further additives, components, integers or steps.

Further aspects of the present invention and further embodiments of the aspects described in the preceding paragraphs will become apparent from the following description, given by way of example and with reference to the accompanying drawings.

BRIEF DESCRIPTION OF THE DRAWINGS

FIGS. 13A and 13B provide partial top views of light directing assemblies in accordance with further alternative embodiments of the invention.

FIG. 13C provides an elevation depiction of a path length adjustment assembly.

DETAILED DESCRIPTION OF THE EMBODIMENTS

Embodiments of the present invention provide system and methods for characterising eye-related systems. Characterisation of an eye related system may involve making observations of the eye-related system and/or taking measurements of the eye-related system.

The term "eye-related system" is used herein to describe a variety of ocular systems such as human or animal eyes, either alone or in association with prosthetic lenses and with or without surgical or other modification, or physical eye models or simulated eyes with or without modification to simulate optical disorders and/or corrective measures.

Figure 1:
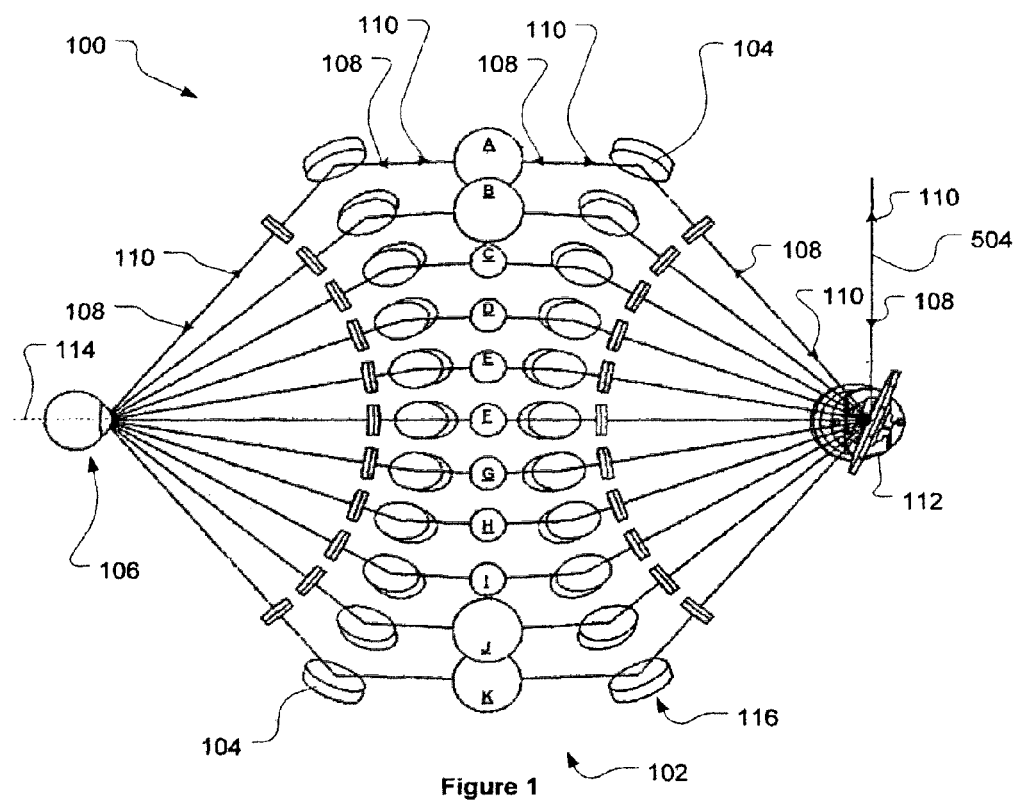
FIG. 1 is a partial top view of an observation and measurement system including a light directing assembly in accordance with an embodiment of the invention.
Figure 2:
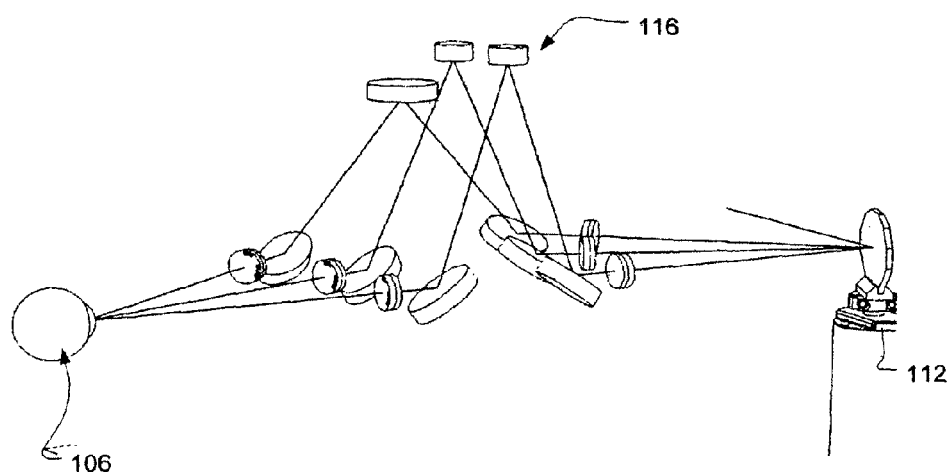
FIG. 2 is a perspective view depicting part of the light directing assembly of the system of FIG. 1.

FIGS. 1 and 2 respectively provide partial top and perspective views of an observation and measurement system 100 in accordance with one embodiment of the invention. In this embodiment system 100 is depicted in use in characterising an eye-related system 106 (the eye-related system 106 not, of course, itself being part of the system 100).

System 100 includes a light directing assembly 102 made up of a plurality of optical elements 104 arranged in an array of optical relay assemblies 116. The plurality of optical elements 104 in the light directing assembly 102 are arranged to direct interrogation beams from a light transmission system (discussed below) to an eye-related system 106, and to direct return beams from the eye-related system 106 to a beam detection system (discussed below).

Interrogation beams are indicated by arrow-heads 108 and return beams by arrow-heads 110. In the present embodiment the interrogation beams 108 are directed from the illumination source to the optical elements 104 of the light directing assembly 102 by a scanning mirror 112 located on an optical axis 114 of the system 100. In the illustrated embodiment the interrogation beams 108 are directed from the scanning mirror 112 to the light directing assembly 102 on the same scanning plane that the interrogation beams are directed from the light directing assembly 102 to the eye-related system 106. The return beams 110 are directed from the optical elements 104 to the beam detection system by the same scanning mirror 112. As discussed in further detail below, however, alternative arrangements are possible.

The interrogation/return beams are directed by the light directing assembly 102 such that they enter/return from the eye-related system 106 at a plurality of interrogation angles. As described in further detail below, the interrogation beams 108 will typically be directed in sequence from one optical relay assembly 116 to the next, thereby sequentially generating the interrogating beams 108 and return beams 110. The optical elements 104 of each optical relay assembly 116 are arranged so as to provide for a predetermined optical path length, relationship between the optical path lengths of the interrogation (and hence return) beams at each interrogation angle. By way of example, the predetermined optical path length relationship may be that the optical path lengths of the interrogation/return beams at each interrogation angle are equal.

Each optical relay assembly 116 of the present embodiment includes a plurality of optical elements 104 that function to (i) deflect an illuminating beam from a light source (see below) as an interrogation beam into the eye-related system 106 and to (ii) deflect the reflected or back-scattered return beam from the eye-related system 106 to a detector means (see below). The angle of the interrogation beam relative to the optical axis 114 is determined both by positions and angles of the optical elements 104 in each optical relay assembly 116. In this way, system 100 can be configured to interrogate an object (such as the eye-related system) at peripheral angles up to and in excess of 50°, of 90°, or even up to around 180°. One non-limiting application of the system 100 is in characterising eyes, in which angles of between 10° and 40° degrees will normally be adequate.

In this particular embodiment eleven optical relay assemblies 116A to 116K are provided (for clarity, in FIG. 1 relay assemblies 116A to 116K are represented by letters "A" to "K" appearing on the central optical element of the relevant relay assembly only). One optical relay assembly 116F is located on the optical axis 114 of the eye-related system 106 and the remaining ten optical relay assemblies extending symmetrically and laterally on either side of the optical axis 114 (relay assemblies 116A to 116E spreading out on one side of the central assembly 116F, and relay assemblies 116G to 116K spreading out on the opposite side of the central assembly 116F). The interrogation angles provided by the optical relay assemblies illustrated range from approximately −50° to +50° (measured from the optical axis 114) by 10° increments (i.e. interrogation angles of −50°, −40°, −30°, −20°, −10°, 0°, +10°, +20°, +30°, +40°, and +50°. It will be appreciated that in alternative embodiments of the system 100, and according to the application in question, a greater or lesser range of field angles may be provided for, and/or with increments of greater or lesser magnitude.

The optical elements 104 of the light directing assembly 102 are arranged such that the interrogating beams between the scanning mirror and the light directing assembly 102 are substantially co-planar, as are the interrogation beams between the light directing assembly 102 and the eye-related system 106. This allows one meridian—the horizontal in the illustrated example—of the eye-related system 106 to be investigated. The common plane of the interrogating beams at the point of contact with/entry into the eye-related system 106 will be referred to as the scan plane of the system 100. Non-horizontal meridians (scan planes) and polar angles of the eye-related system 106 may be investigated by simply rotating the assembly 100 (or the relevant components thereof) about the optical axis 114 of the eye-related system 106. To facilitate such rotation, and in some embodiments, the system 100 (or the relevant components thereof) may be mounted on gimbals or a pivoting axis to allow the system 100 to swivel/turn about its optical axis so as to allow observation/measurement of vertical and/or oblique axes/meridians.

Figure 3:
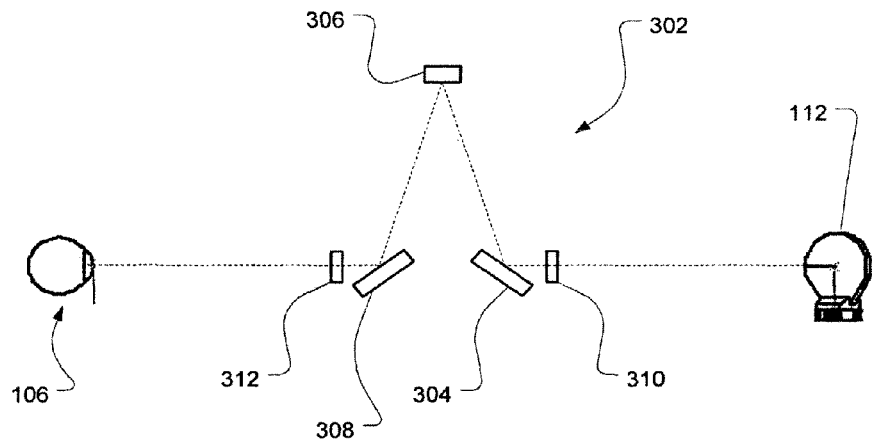
FIG. 3 is an elevation depiction of an optical relay assembly of the light directing assembly depicted in FIG. 1.

FIG. 3 provides an elevation depiction of a single optical relay assembly 302 (optical relay assembly 302 typifying each of the eleven optical relay assemblies 116 shown in FIG. 1) in accordance with one embodiment of the invention. As can be seen, optical relay assembly 302 includes three primary optical elements: a source-proximate element 304, a central element 306, and an eye-related system-proximate element 308. In addition, on either side of the source- and system-proximate elements 304 and 308 the system 100 of the present embodiment includes source- and system-proximate relay elements 310 and 312 respectively. Relay elements 310 and 312 are relay lenses which capture and refocus the interrogation/return beams in order to reduce excessive increase in the beam diameters.

In alternative embodiments, the combination of the source-proximate relay 310 and element 304 could be replaced with a single optical element in the form, for example, of a non-spherical (astigmatic) concave mirror. This is also the case for the distal-proximate relay 312 and element 308. The optical relay assembly 302 relays (or directs) interrogation beams 108 from the scanning mirror 112 to the eye-related system 106 and return beams 110 from the eye-related system 106 to the scanning mirror 112. More specifically:

the source-proximate element 304 is arranged to direct an interrogation beam 108 from the scanning mirror 112 to the central element 306, and to direct a return beam 110 from the central element 306 to the scanning mirror 112;

the central element 306 is arranged to direct an interrogation beam 108 from the source-proximate element 304 to the eye-related system-proximate element 308, and to direct a return beam 110 from the eye-related system-proximate element 308 to the source-proximate element 304; and the eye-related system-proximate element 308 is arranged to direct an interrogation beam 110 from the central element 306 to the eye-related system 106, and to direct a return beam from the eye-related system 106 to the central element 306.

In the present embodiment, the source-proximate elements 304 are arranged along the same transmission plane in order to direct interrogation/return beams from/to the scanning mirror 112 in the same plane (i.e. the portions of the interrogation/return beams travelling between the scanning mirror 112 and source-proximate elements 304 are co-planar). In this instance the transmission plane is co-planar with the scan plane of the system 100. Similarly, the eye-related system-proximate elements 308 are arranged along the same plane so as to direct interrogation/return beams from/to the eye-related system 106 in the same plane (i.e. the portions of the interrogation/return beams travelling between the eye-related system-proximate elements 308 and the eye-related system 106 are co-planar along the scan plane of the system). The central elements 306, however, are not co-planar with the scan plane of the system. Rather, the central elements 306 lie in a plane that is perpendicular to the scan plane. As such, between the source-proximate elements 304 and eye-related system-proximate elements 308 the interrogation/return beams leave the scan plane of the system as they are directed to/from the central elements 306.

Figure 4:
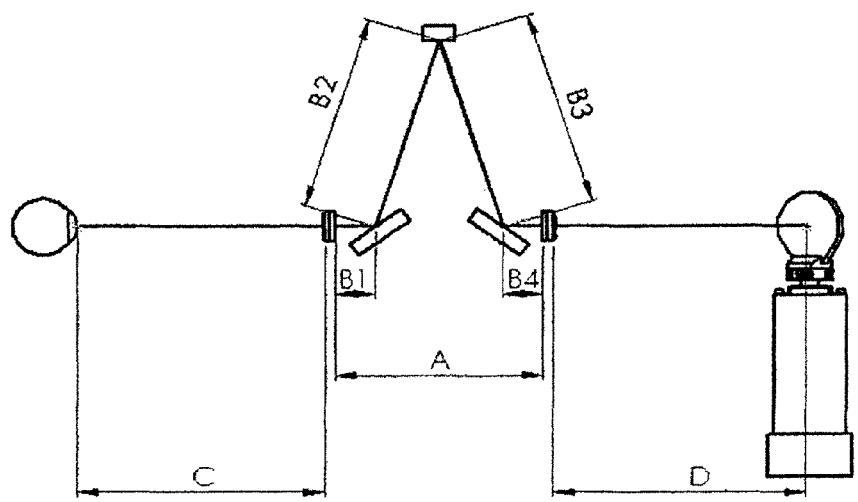
FIG. 4 is a schematic representation of an optical path provided by the optical relay assembly of FIG. 3.

As can be seen in FIG. 1, the source-proximate relays 310 of each optical relay assembly are equidistant from the scanning mirror 112 (by being radially arranged/positioned relative to the scanning mirror 112). Similarly, the eye-related system-proximate relays 312 of each optical relay assembly are equidistant from the eye-related system 106 (again by radial arrangement of the eye-related system-proximate elements). By arranging the optical elements 104 in this manner, and referring to FIG. 4, for each optical relay assembly 116 in the light directing assembly 102: optical distance D (between the scanning mirror 112 and each source-proximate relay 310) is the same; and optical distance C (between the eye-related system 106 and each eye-related system-proximate relay 312) is the same.

For each optical relay assembly 116 in the light directing assembly 102, however, the physical distance A (between the source-proximate and eye-related system-proximate relays 310 and 312) varies in accordance with the interrogation angle provided by that relay assembly. In order to provide for a predetermined optical path length relationship between the optical paths of each optical relay system 116A to 116K, (i.e. path D→B4→B3→B2→B1→C in FIG. 4), the position of one or more of the optical elements of each optical relay assembly 116 can be adjusted as required. Typically, the optical element that will be adjusted in order to provide the path length relationship will be the central optical elements 306 (serving to adjusting distances B2 and B3), though in addition, or alternatively, the position source-proximate elements 304 and/or the eye-related system-proximate elements 308 may be adjusted (serving to adjust distances B4 and B1 respectively). As noted above, the position of the central optical elements 306 may be adjusted in a plane that is normal to the scan plane of the system 100.

In the context of the present embodiment (i.e. evaluating eye-related optical systems), the predefined optical path length relationship will typically be that the path length D→B4→B3→B2→B1→C of each optical relay assembly 116A-K (i.e. at each interrogation angle) is equal. By way of non-limiting example, the distances between the various optical elements may be as follows (all values in mm):

| Optical relay assembly | Distance D | Distance B4 | Distance B3 | Distance B2 | Distance B1 | Distance C | Total distance |
|---|---|---|---|---|---|---|---|
| 116A | 97.419 | 32.08 | 65.9475 | 65.9475 | 32.42 | 97.079 | 390.893 |
| 116B | 97.419 | 25.08 | 72.9475 | 72.9475 | 25.42 | 97.079 | 390.893 |
| 116C | 97.419 | 21.08 | 76.9475 | 76.9475 | 21.42 | 97.079 | 390.893 |
| 116D | 97.419 | 15.58 | 82.4475 | 82.4475 | 15.92 | 97.079 | 390.893 |
| 116E | 97.419 | 15.58 | 82.4475 | 82.4475 | 15.92 | 97.079 | 390.893 |
| 116F | 97.419 | 15.58 | 82.4475 | 82.4475 | 15.92 | 97.079 | 390.893 |
| 116G | 97.419 | 15.58 | 82.4475 | 82.4475 | 15.92 | 97.079 | 390.893 |
| 116H | 97.419 | 15.58 | 82.4475 | 82.4475 | 15.92 | 97.079 | 390.893 |
| 116I | 97.419 | 21.08 | 76.9475 | 76.9475 | 21.42 | 97.079 | 390.893 |
| 116J | 97.419 | 25.08 | 72.9475 | 72.9475 | 25.42 | 97.079 | 390.893 |
| 116K | 97.419 | 32.08 | 65.9475 | 65.9475 | 32.42 | 97.079 | 390.893 |

By making the optical path length for each interrogation angle the same, relatively sharp focus can be maintained across all interrogation angles, and accurate measurements can be made from reflected wavefronts or images. This is in contrast, for example, to the system described in WO 2008/116270 in which the optical path lengths vary between different interrogation angles, hindering focussing and accurate measurement. By maintaining a sharp focus of the anterior eye-related system between all interrogation angles, a more accurate alignment of the instrument axis with the pupil centre can be achieved. This is of significant importance for accurate refraction and wavefront measurements (as demonstrated, for example, by C. Fedtke, K. Ehrmann, A. Ho, B. Holden. Lateral pupil alignment tolerance in peripheral refractometry. Optom Vis Sci. 2011; 88:E570-579, AAO paper 2010).

In the illustrated embodiment, the optical system between the eye and the scanning mirror is essentially symmetric, i.e. the path lengths, mirror angles, and focal lengths of the relays lenses are substantially the same on the left and right hand sides. While there are optical advantages in such a symmetrical or substantially symmetrical design (in that optical distortions and aberrations of the relay/mirror system are reduced), such symmetry is not essential.

In alternative embodiments, the predetermined path length relationship may be such that a difference in optical path lengths at various interrogation angles exist. This may be implemented, for example, in order to offset any anticipated bias between the different field angles of the object being observed, thereby reducing the required dynamic range of the system 100. For example, a particular eye related system could have a generally more myopic refraction in the periphery compared to the central refraction—e.g. 2.00 D more myopic at ±50° than at 0°. In this case the optical path length at these two angles could be adjusted so that a wavefront detector measures the same refraction as in the centre. To obtain the actual measurement result, the 2.00 D is subtracted from the wavefront detector reading. The measurable dynamic range is therefore increased by 2.00 D.

As discussed in greater detail below, alternative arrangements of the optical relay assemblies are, of course, possible.

A variety of optical elements 104 could' suitably be used in the light directing assembly 102. Typically the optical elements 104 will be mirrors (specifically plano mirrors) which are not prone to dispersion and/or chromatic effects. Alternative optical elements, such as prisms, non-spherical (astigmatic) concave mirrors and suchlike could also/alternatively be used.

Figure 5:
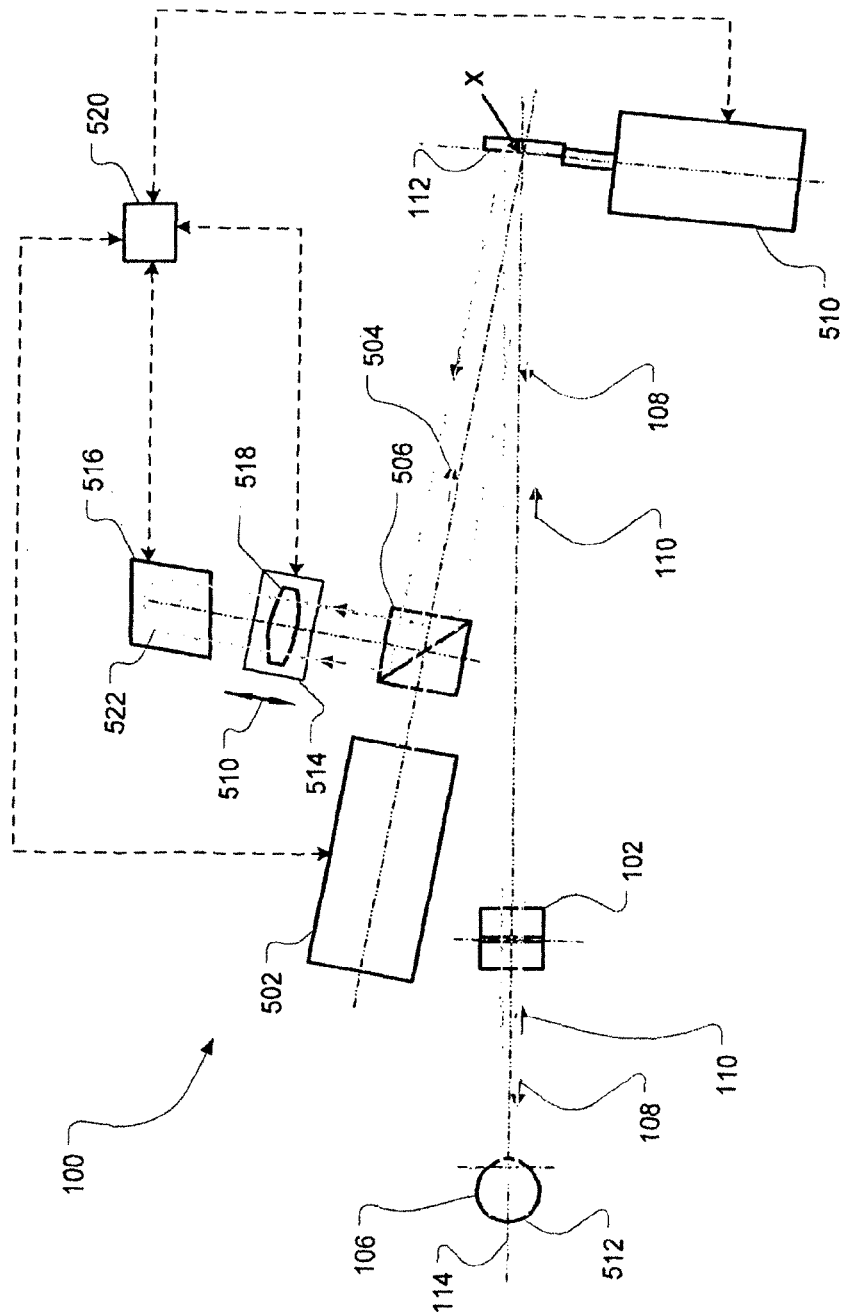
FIG. 5 is a diagrammatic plan of an observation and measurement system in accordance with an embodiment of the invention.

Turning to FIG. 5, a diagrammatic plan of a system 100 utilising the light directing assembly described above is shown. It will be appreciated, however, that many variations (and alternatives) to system 100 are possible, two of which are described by way of non-limiting example below and with reference to FIGS. 8A and 8B.

System 100 includes a light source 502 which directs a collimated source beam 504 via a beam-splitter 506 to a light transmission system which, in this instance, is oscillating scanning mirror 112 which transmits light from a light source. Scanning mirror 112 is moved by actuator 510 to generate illuminating or interrogation beams 108 which are scanned between successive light relay assemblies 116 in the light direction assembly 102 to generate a sequence of interrogation beams 108 that are directed into eye-related system 106 and onto the retina 512 over the desired range of incident angles. Scanning mirror 112 thus forms a point source or common point for the interrogation beams 108 and a common point (indicated at X) for all return beams 110. Thus, each return beam 110 returned from retina 512 passes back via the light directing assembly 102 and scanning mirror 112 to beam-splitter 506 by which it is diverted via a focusing system 514 to a photo detector 516. Focussing system 514 includes a moveable lens assembly 518 that can be moved axially back and forth through a focus range, as indicated by arrows 510. The source beam 504 (and, thus, the interrogating and return beams 108 and 110) can have any desired spot, disc or annular cross-section desired. In some applications, beams of an annular cross-section like that commonly used in known autorefractors (such the Shin-Nippon SRW-5000) may be appropriate as they can be analysed and processed in a substantially standard manner. As described below with reference to FIG. 8B, in alternative embodiments the photo detector 516 is replaced by a wavefront sensor, such as a Hartmann Shack or equivalent system, which can determine both refraction and higher order aberrations.

In many instances it is preferable to generate the interrogation beams 108 one at a time so that the total intensity of the light entering the eye-related system 106 being examined at any instant is minimised. Sequential generation also enhances the ability of the detector 516 to discriminate between return beams 110. However, scanning an illuminating beam from one optical relay assembly 116 to the next is not essential as sequential generation of interrogation beams can be achieved in other ways—e.g. by the use of electronic shutters before and/or behind the array or by use of moveable beam deflector elements. With any of these, a rapid sequence of interrogation beams can be generated over a wide range of interrogation angles, the speed of scan being largely determined by the rate at which return beams can be detected and the associated data recorded. Scanning and detection are preferably conducted automatically by or under the control of computing system, such as computer processing system 520 discussed below or an alternative digital processor/controller.

Often, rapid scanning is desirable as it allows good fixation of a live natural eye throughout a procedure. The system allows optical characteristics of the eye-related system to be computed and mapped substantially in real-time, with the entire interrogation and detection sequence taking place over a period of a few seconds. Embodiments the system may be configured/operated such that interrogation and detection sequence takes place in less than one second, in less than 0.5 seconds, and/or between 0.1 and 0.2 seconds.

Where scanning is thought to be speed-limiting, a few beam deflection elements may be illuminated at once to generate multiple simultaneous return beams that will need to be distinguished for separate detection. This can be done by using electronic shutters to chop or pulse-code one or more of the return beams. Selective polarisation may also be employed to distinguish the return beams, which can also be implemented by a suitable electronic shutter serving as a selective polariser. By way of alternative, selection may also be made by a poly-chromatic interrogation beam, a band pass filter in each interrogation/return path, or by a rotating wheel located in the common return path and containing a plurality of filters.

While the present embodiment uses a scanning mirror 112 as a light transmission system, the transmission of interrogating beams 108 one at a time into eye-related system 106, and the generation of a corresponding sequence of return beams 110, could be effected in a variety of ways. First (as will be described below), the light transmission system may include a beam scanner that directs a single narrow illuminating beam from one optical relay assembly 116 to another. Second, multiple optical relay assemblies 116 could be illuminated at one time and downstream interrogating beams 108 gated to effect scanning of eye-related system 106 and the generation of a sequence of return beams 110. This could be done, for example, by inserting an electronically controllable LCD shutter between the optical relay assemblies 116 and the eye-related system 106 and using it as scanning means by which interrogation beams 108 from the optical relay assemblies 116 are admitted into eye-related system 106 one at a time. Thus, it is not essential for the light transmission means to include scanning means and it is possible to distribute the scanning function between a scanning means and/or shutters or the like.

In this way, successive interrogation/return beam pairs diverge/converge at successively larger/smaller angles with respect to axis 114 as they pass into and out of the eye-related system 106. In many situations sequential scanning from one angle to the next adjacent angle (i.e. from one optical relay assembly 116 to the adjacent optical relay assembly 116) may be convenient, but many other scan sequences may be used to minimise biases that might arise due to fixed sequential scanning. While illumination of more than one optical relay assembly 116 at a time can easily be achieved by use of a scanner such as scanning mirror 112, if this is done it is then necessary to distinguish the multiple simultaneous return beams that result. This can be done by using a shutter as a beam-chopper (or other means such as a selective polariser, chromatic keying, and/or chromatic filter elements) to differentially encode each return beam that needs to be distinguished from another at the detection system.

By way of example, two refraction techniques will be described.

Ring type auto-refractor: As each return beam 110 is being received, focusing lens assembly 514 is moved along the direction of the optical axis to vary the focus of the image 522 received at the detector 516. Commonly, three positions of the image telecentric focussing assembly 514 may be recorded for each of three return beam image focuses: one position where the image (spot or ring) appears in sharpest focus, a second position where the image appears optimally focussed in one meridian and a third position where the image is optimally focussed in a different meridian, usually one that is orthogonal to the first meridian. The three positions of lens assembly 514 respectively are indicative of the spherical equivalent power of the eye-related system 106, the sagittal astigmatic component and the tangential astigmatic component of the refraction. Although the position of the focussing assembly is indicative of the spherical and/or cylindrical equivalent power of eye-related system 106, it may be preferable to determine power by observing the size of the image formed on the retina 512. The significance of spot/image size in relation to spherical equivalent power of eye-related system 106 can be understood in the following elementary way. Should the interrogating beam 108 that enters eye-related system 106 be converging, a normal or emmetropic eye-related system 106 will form a nominally sized image on retina 512. A myopic eye-related system 106, however, will form a larger than nominal sized image and a hyperopic eye-related system 106 will form a smaller than nominal sized image.

Aberrometer: As each return beam 110 is being received, focusing lens assembly 514 is moved along the direction of the optical axis to provide precompenstaion of the wavefront defocus, reducing the wavefront defocus to a range measurable by detector 516. Commonly, the position of the focussing assembly 514 is recorded and accounted for when determining refractive status of eye related system 106. Detector 516 may be a wavefront sensor such as a Hartmann Shack or other equivalent sensor or system.

System 100 also includes a computer processing system 529 that is connected to receive and analyse the output of detector 516 and to control the various components of the system 100.

Figure 6:
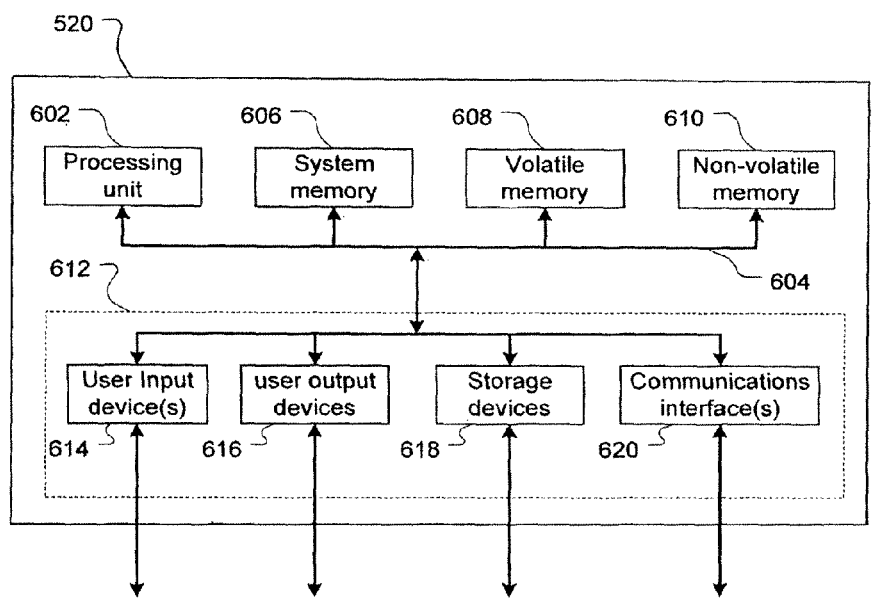
FIG. 6 is a block diagram of an embodiment of a computing device suitable for use with observation and measurement systems according to embodiments of the present invention.

By way of example, FIG. 6 shows a block diagram of a computer processing system 520 suitable for use with system 100. The computer processing system 520 includes at least one processing unit 602. The processing unit may include a single processing device (e.g. a microprocessor or other computational device), or may include a group or cluster of processing devices. Additionally, the processing unit may include local processing devices only, or may include distributed processing devices accessible and useable (either in a shared or dedicated manner) by the system 520.

A communications bus 604 provides for communication (i.e. data transfer) between various components of the system, such as the processing unit 602, a system memory 606, volatile memory 608 (e.g. random access memory including one or more DRAM modules) and non-volatile memory 610 (e.g. one or more hard disk drives, solid state disk drives, or other non-volatile storage devices). A basic input/output (BIOS) stored, for example, in the system memory 606 may provide the basic routine that helps to transfer information between components within the system 520, such as during start-up.

The computer processing system 520 also includes one or more input/output interfaces 612 by which peripheral devices can be connected to the computer processing system 520. As will be appreciated, a wide variety of peripheral devices may be used, including intelligent input/output devices having their own memory and/or processing units. By way of non-limiting example, the system 520 may provide interfaces to allow for the connection of: one or more user input devices 614 (e.g. a keyboard, mouse, microphone, touch-screen etc); one or more user output devices 616 (e.g. a display unit such as a CRT, LCD or LED screen and/or speakers); and one or more storage devices 618 (e.g. hard disk drives, solid state disk drives, CDs (via a CD drive), DVDs (via a DVD drive), Blue-Ray discs (via a Blue-Ray drive), flash memory devices, etc).

In the present embodiment, the processing system 520 is also in communication with the additional peripheral devices of the detector 516 (to receive the detected data), lens assembly 518 (to allow control thereof under the servo-control) and the actuator 510 (to allow control of the scanning mirror 112 to ensure correct timing of illumination and return signal detection). A connection between light source 502 and the processing system 520 is also provided as it will generally be convenient to ensure that source beam 504 is correctly configured and that a representation of the current source beam sectional pattern is stored for comparison with image 522 captured at the photo detector 516.

The actual connection of peripheral devices may be achieved using standard connection interfaces with standard data transfer protocols, such as serial connections, parallel connections, e-Sata connections, USB connections, FireWire connections etc. Alternatively, some peripheral devices may use unique connectors and/or data transfer protocols.

System 520 also includes at least one communications interface 620 which may, for example, be a Network Interface Card allowing for wired or wireless connection to a network. Communication with a network (and other devices connected thereto) will typically be by the protocols set out in the layers of the OSI model of computer networking. For example, applications/software programs being executed by the processing unit 602 may communicate using one or more transport protocols, e.g. the Transmission Control Protocol (TCP, defined in RFC 793) or the User Datagram Protocol (UDP, defined in RFC 768).

The optical elements 104 of the light directing assembly 102 may be fixedly mounted in position in the light directing assembly 102. Alternatively, some or all of the optical elements 104 may be mounted on actuators to allow the angle and/or position of the optical elements 104 to be changed. In this case the actuators would typically be in communication with the processing system 520 to allow control of the actuators (and, thereby, the position/angle of the optical elements 104 by the processing system 520). A variety of actuators may be used, e.g. solid-state devices such as barium titanate piezoelectric actuators.

If desired, the source beam path 504 may be spatially separated from the observation path (i.e. the path of the return beams to detector 516) by one or several step angles by positioning the detection system at a different angle to from the source beam at the scanning mirror 112. This may be useful, for example, if the system is to be used in a slit lamp like application or for Scheimpflug photography.

In use, refractive error and other aberrations of the eye-related system 106 can be determined and, if desired, mapped onto a surface by comparing the interrogation beam with its corresponding return beam for each optical relay assembly. This may be done by comparison of wavefronts, relative displacement, angle, position or cross-sectional shape. Since the source and interrogation beams will have substantially identical optical properties, it may be convenient to use the source beam as a proxy for the interrogation beam in such comparisons. Indeed, it will normally be sufficient to store data concerning the source beam as a basis for such comparisons. Reference to comparing a return beam with an interrogation beam should therefore be understood to include comparison of a return beam with data concerning the source beam.

Figure 7:
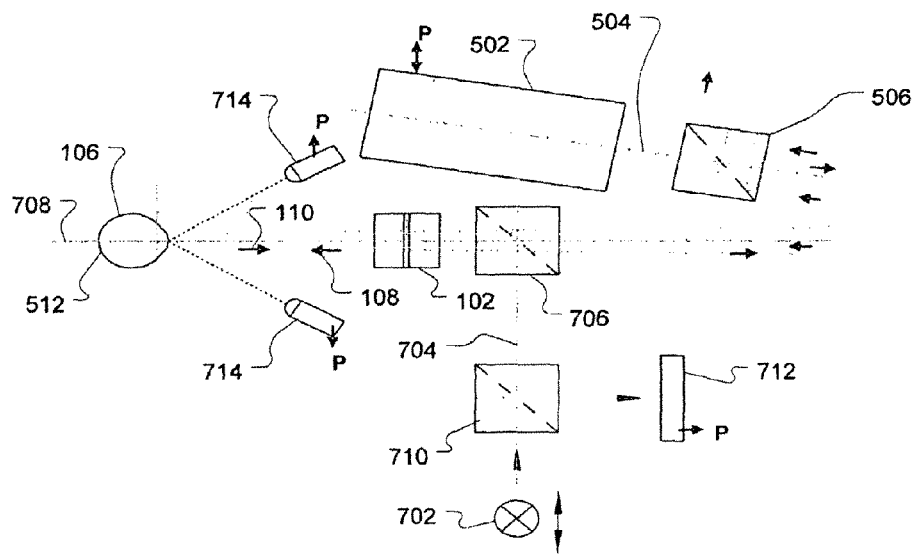
FIG. 7 is an enlarged partial view of the observation and measurement system of FIG. 5 depicting additional features/refinements.

FIG. 7 is an enlarged partial view of the system 100 shown in FIG. 5 including additional features/refinements. In the embodiment of FIG. 7 system 100 further includes a movable fixation target 702 located on a gaze beam path 704 that is optically coupled by a first additional beam-splitter 706 into return beam path 110 and on optical axis 114. Fixation target 702 aligns the gaze or axis of the eye-related system 106 with the optical axis 704 on which the system 100 is positioned and controls accommodation. A second additional beam-splitter 710 in gaze path 704 directs an image of the eye-related system 106 onto a detector 712 (e.g. a CCD), allowing gaze direction and eye-alignment to be monitored. Optical or acoustical distance sensors 714 can be used to (alternately or additionally) indicate when the eye-related system 106 appears to be axially aligned. Typically, the sensors 714 and detector 712 are connected to the processing system 520—as indicted by arrows marked P—so that initiation of a measurement cycle can be automatic once fixation is confirmed. Fixation target 702 (or an actuator controlling movement thereof) may also be connected to the processing system 520 to allow the position of the target 702 to be automatically adjusted if desired.

By using a fixation target that can be moved/switched between different distances along the optical axis, the system can enable refraction measurements under various states of accommodation to be taken.

Figure 8A:
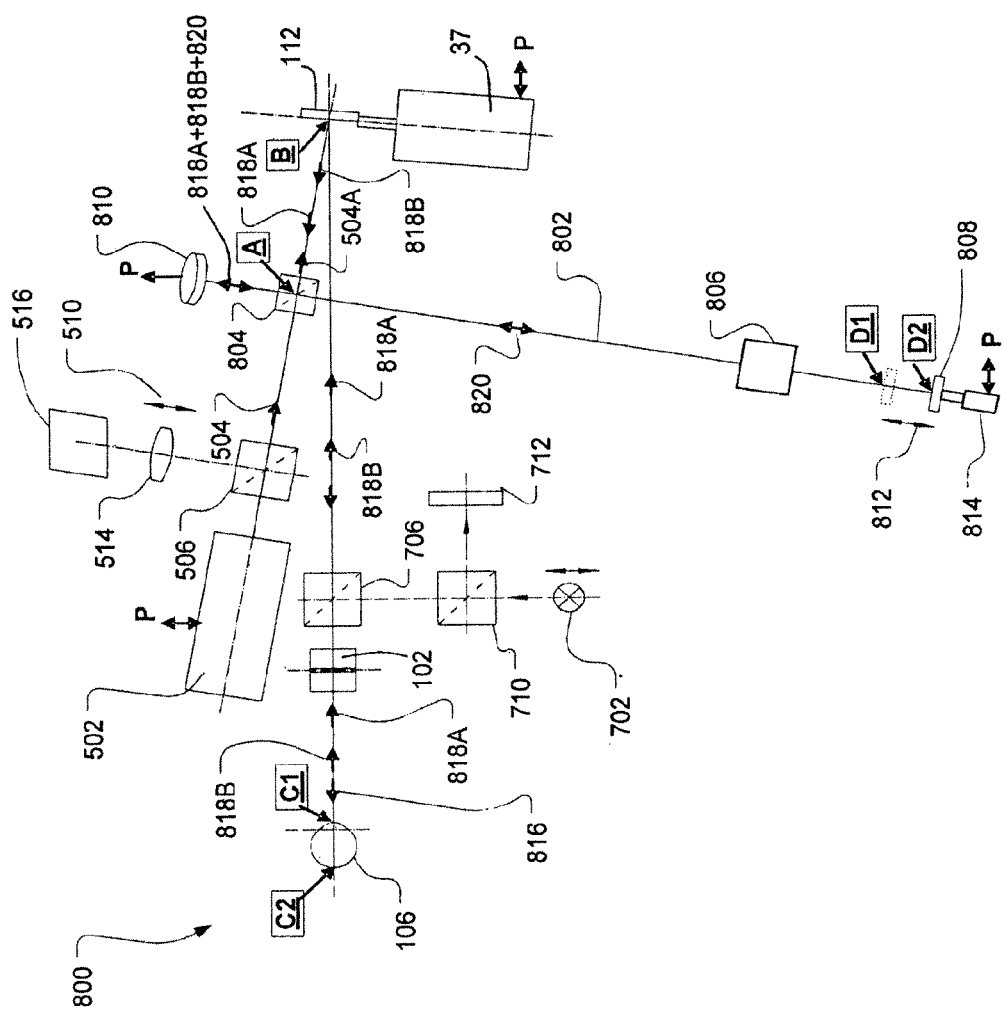
FIG. 8A is diagrammatic side elevation view of an observation and measurement system in accordance with a further embodiment of the invention.
Figure 8B:
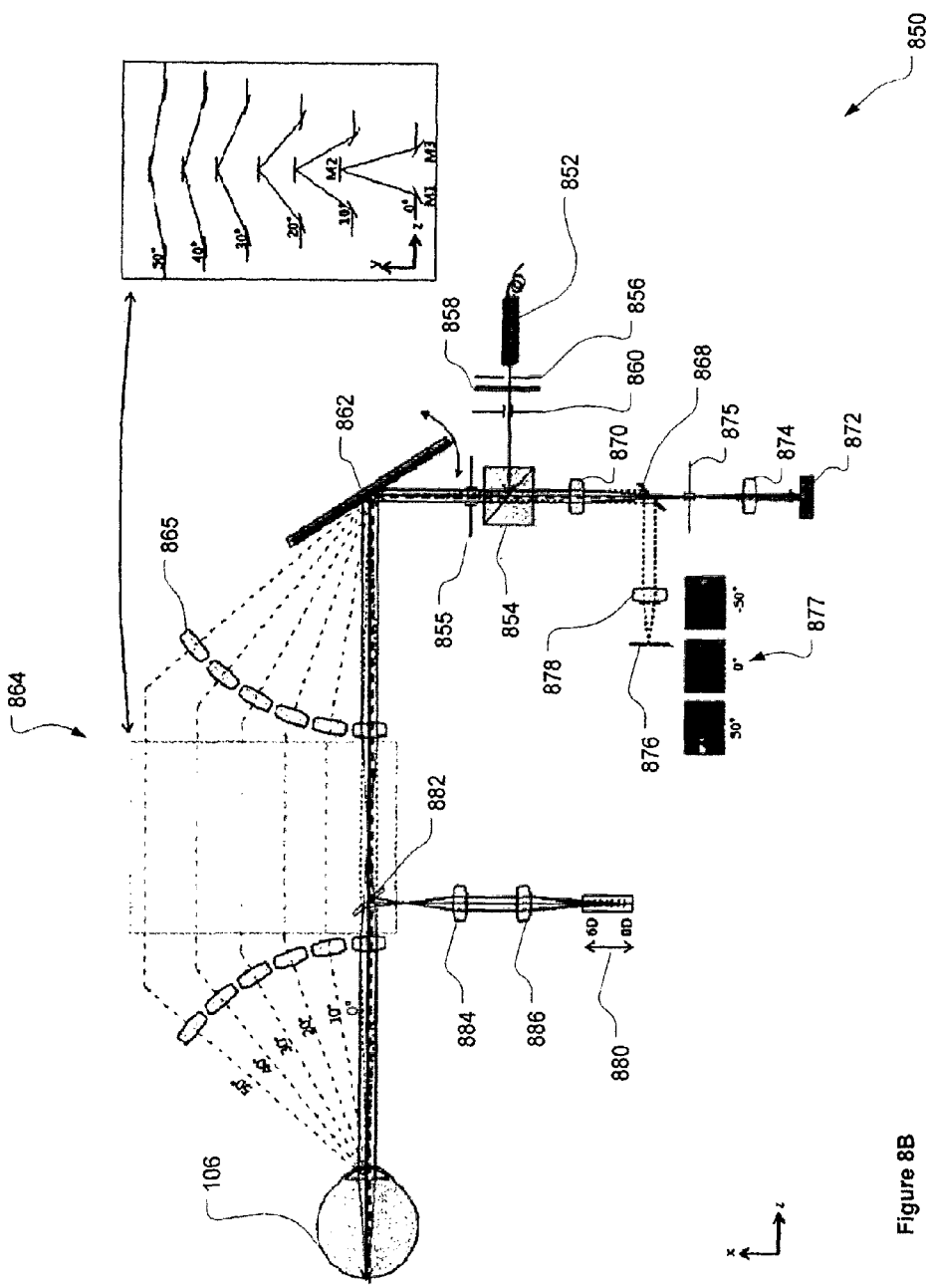
FIG. 8B is diagrammatic side elevation view of an observation and measurement system in accordance with a still further embodiment of the invention.

FIGS. 8A and 8B provide diagrammatic side elevation views of observation and measurement systems 800 and 850 in accordance with further embodiments of the invention.

System 800 of FIG. 8A includes many of the components of system 100 (with like reference numerals adopted where appropriate), however further includes an interferrometer beam path 802 for the measurement of eye length.

The interferrometer beam path 802 is arranged substantially at right angles to the source beam 504 that is emitted by low coherence light source 502. It includes (i) an additional beam-splitter 804 arranged in beam 504 before scanning mirror 112, (ii) a dispersion compensation element 806, (iii) an additional moveable mirror 808 and (iv) an additional photo detector 810 (connected to the computer processor 520 as indicated by arrow P). As indicated by arrows 812, mirror 808 is moveable along beam path 802 toward and away from beam splitter 804, by an actuator 814 under the control of processing system 520 (the connection to which being indicated by arrow P). Preferably, actuator 814 is operated to reciprocate mirror 808 back and forth.

System 850 of FIG. 8B also includes many of the components of system 100 (with like reference numerals adopted where appropriate). In system 850 the light source 852 is a superluminescent diode (SLD) which directs a source beam to a beam-splitter 854 via a shutter 856, a polariser 858, and an aperture 860. Beam splitter 854 directs the source beam to an oscillating scanning mirror 862 (via, in this instance, an aperture 855) which, in turn, transmits light to the light directing assembly 864. Light directing assembly 864 (only partially shown) may be a light directing assembly in accordance with one of the embodiments of the present invention. As with the above systems, scanning mirror 862 generates illuminating/interrogation beams which are scanned between successive light relay assemblies (or, more particularly, the source-proximate relay elements 865 of successive light relay assemblies) in the light direction assembly 864 to generate a sequence of interrogation beams that are directed into eye-related system 106.

The eye-related system 106 generates return beams which are directed back to beam splitter 854 by the light directing assembly 864 and scanning mirror 862. Beam-splitter 854 directs the return beams to a further beam splitter 868, via relay lens 870.

Beam splitter 868 directs return beams to a wavefront sensor 872 (in this case a Hartmann-Shack Sensor) via relay lens 874 and aperture 875. One advantage of the light directing assembly 864 (as has been described above) is that the optical path length for each scanning angle may be kept equal or in a predefined relationship to the other optical path lengths for each scanning angle. This reduces focussing requirements and allows for use of a wavefront sensor 872 which can be used to provide information on both refraction and higher order aberrations in the eye-related system 106. Given the reduced focussing requirements provided by the light directing assembly 864, a focussing lens system (such as system 514 of the embodiment of FIG. 5) is not strictly necessary, though may be included to increase the dynamic range of the system.

Beam splitter 868 also directs return beams to a photo detector 876 (in this case a CCD), via focussing lens 878. Photo detector 876 can, in turn, be linked to one or more pupil alignment screens 877 for use in monitoring gaze direction, lateral eye-alignment, axial eye-alignment, pupil diameter, and/or line of sight.

System 850 also includes a movable fixation target 880 located on a gaze beam path that is optically coupled by beam-splitter 882. Beam splitter 882 is positioned on the optical axis of the eye-related system 106 and directs a gaze beam to the target 880 via relay lenses 884 and 886.

The various components of system 850 are in communication with a computer processing system (not shown) for data transfer and/or control. As will be appreciated, not all elements of system 850 may be necessary for all applications. By way of one, non-limiting example, while apertures 860, 855, and 875 have been used in the illustrated embodiment to improve beam quality, they may not be necessary in alternative embodiments.

In ocular applications, an interrogation beam will encounter multiple interfaces between materials of different optical characteristics as it travels into the eye-related system, and therefore the respective return beam will be composed of a set of component return beams. The component return beams which are generally of most interest are those returned from the anterior cornea and the retina (the rear-most interface of the eye-related system) because these correspond to the length of the eyeball. Fortunately, the component beams returned from the cornea and retina are also usually the most intense and/or distinct. While component beams returned from other surfaces within the eye-related system are more difficult to detect and distinguish from one another, the technique of the present invention allows for such component return beams to be selected for analysis. Selection and comparison of return beam components associated with both the cornea and the retina will allow the length of the eye to be determined using interferometric methods, eye length being of critical interest for the monitoring of myopia progression.

Interferometric measurement of eye length may be combined with the mapping of refractive aberrations of an eye with particular advantage where a scanning illuminating beam is generated from a source beam at a single or common point, as by the use of a moving scanning mirror. This allows each return beam with its retina and cornea components to be returned to a common location where aberrations and cornea-retina distance can be determined for every return beam. The common location is the source beam prior to the scanning point where the return beams can be coupled into a detector beam path and an interferometer beam path using beam-splitters. To measure retina-cornea distance, a reference beam (part of the source beam) is also coupled into the interferometer beam path so that it can interfere with the return beam components in a manner that can be detected, interference being created by changing the length of the interferometer beam path in such a way that the length of the reference beam relative to the return beam in that path is changed. This change in length can be effected by moving a mirror and monitoring for interference, the distance the mirror moves being related to the retina-cornea distance, though not identical. To achieve interference in this way the reference beam (and therefore the source beam) is preferably of low coherence, substantially monochromatic and preferably in the near infra-red.

It will be assumed in what follows that the axial length of eye-related system 106 is of interest. Accordingly, and with reference to system 800 of FIG. 8A, axial interrogation beams 816 (i.e. an interrogation beam aligned with the optical axis of the eye-related system 106) and corresponding return beams 818 (including return beam portions 818A and 818B are those under consideration. In use, source beam 504 travels through additional beam-splitter 804 and is split at point A into two emerging beam portions, beam 504A which continues (as before described) to scanning mirror 112 and a reference beam 820 that is reflected by splitter 804 into beam path 802 on to reciprocating mirror 808 from which it is reflected back via point A to detector 810. Since the portion of interferometer path 802 between point A and detector 810 is also traveled by return beam portions 818A and 818B, which is reflected to detector 810 by splitter 804, reference beam 820 can interfere or beat with return beam portions 818A and 818B. It is of course necessary that the travel of mirror 808 during reciprocation is sufficient to cause interference between both return beam portions 818A and 818B. These interferences are detected by detector 810 and transmitted to processing system 520 along with the precise position of mirror 808. For convenience, it is assumed that interference with return beam portion 818A occurs when mirror 808 is at point D1 and that interference with return beam portion 818B occurs when mirror 808 is at point D2.

More specifically, the interference will appear if the optical distances [A, B, C1] and [A, D1] or [A, B, C2] and [A, D2] are equal. Since the relative distance between D1 and D2 is accurately known from the mirror positions, the optical distances between points C1 and C2 are also known. The physical distance between cornea and retina surfaces can then be computed by using well known group refractive index values of ocular media to convert the optical distances into physical distances. Measurement accuracy can be improved by the use of the dispersion compensating element 806 into beam path 802, such devices being known in the art and described, for example, in: "Eye-Length Measurement by Interferometry with Partially Coherent Light", A. F. Fercher, K. Mengedoht, and W. Werner, Optics Letters, Vol. 13, Issue 3, pp. 186-188 (1988); and U.S. Pat. No. 7,400,410 B2 titled Optical Coherence Tomography for Eye-Length measurement.

The embodiments of the invention described above provide for systems that can measure and/or observe an object (such as an eye-related system) from different directions and within a very short time frame (e.g. between 0.1 and 0.2 seconds). This can be achieved using a single illumination source and a single observation system both of which maintain equal (or otherwise related) optical path lengths between any of the multiple observation/interrogation angles.

Embodiments of the invention have particular application in measuring and observing eye-related systems, for example in the field of measuring central and peripheral refraction and higher order aberrations of eyes and eye-related systems. By using the light directing assembly (or a variation thereof) more accurate pupil alignment can be achieved compared to known alignment methods. The system may also be used to take a variety of other measurements/observations of an eye-related system, for example:

axial length, anterior chamber depth, and corneal thickness measurements as described above; and corneal curvature and anterior chamber angle measurements, e.g. from anterior segment OCT images generated by readily available OCT instruments.

The system may also be adapted/configured for slit biomicroscopy by using a visible light source passing through a slit, optically conjugate to the cornea. The corneal slit image may be captured using a pupil camera. In this case it may be advantageous to mount the slit illuminator so that it can be pivoted in fixed angular increments, so as to illuminate the cornea from a different angle than it is observed.

Embodiments of the system may also be used to determine the angular displacement between the visual and optical axis of an eye by comparing the observed pupil (or iris) size/shape at 2 or more observation angles while the eye is fixated at a known location. In a relatively simple implementation, two images of the anterior eye may be captured, one at +30° and one at −30°, while the eye fixates centrally. Using either the horizontal pupil or the horizontal cornea diameter, the asymmetry between the two diameters can then be correlated to the horizontal component of optical and visual axis. Similarly, the vertical component can be determined by turning the instrument around its optical axis and mentioned earlier.

Embodiments may also, or alternatively, be used to determine the rotation of an eye-related system (or other object) in a plane coincident to the multiple optical axes by comparing an observed feature (e.g. the elliptical pupil size) at two or more observation angles.

As will be appreciated, however, the features of the light directing assembly as discussed above (allowing for optical path lengths for different interrogation angles to be equalised) may be utilised in other measurement and observation system/instruments. For example, the assembly (or a modification thereof) could be used in slit-lamps, low coherence thickness and length measurement instruments, and ophthalmoscopes.

Further, while the systems above have been described in relation to measuring and observing an eye-related system, features of the systems could also be adapted to measure and observe other objects and/or systems in which taking discrete measurements/observations at a variety of observation (interrogation) angles is desirable. For example, the systems could be adapted for use in multi-directional spectroscopy on biological samples or such like, with various configuration parameters of the systems (e.g. the number of scanning positions, angular range, working distance, precision etc) being optimised as appropriate for a given application, such as use:

to detect the distance and lateral placement and orientation of an object by quasi simultaneous observation from at least 2 different directions;

to describe the detected placement of the object with respect to the instrument by use of a single false colour image formed by overlaying 2 or more of the above-mentioned quasi simultaneous images after colour coding each image individually;

to determine the lateral placement of an object by detecting focus and hence distance along 2 or more observation angles;

to determine the rotation of an object in 2 planes which are perpendicular to the multiple optical axes by observing the projected tilt of the object seen through 2 or more observation angles; and/or to generate stereo images of an object.

Figure 9A:
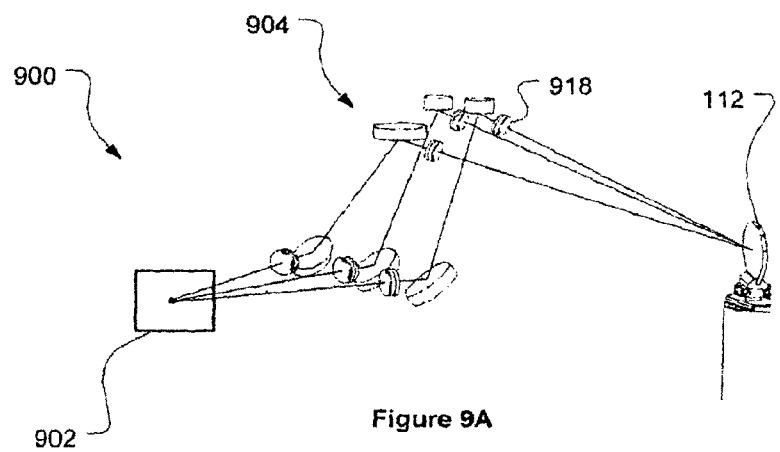
FIGS. 9A and 9B respectively provide partial perspective and elevation views of a light directing assembly in accordance with an alternative embodiment of the invention.

Light directing assemblies in accordance with alternative embodiments of the invention will now be described with reference to FIGS. 9, 10, 11, 12, and 13. These light directing assemblies may be used with the measurement/observation systems described above (e.g. systems 100, 800, or 850), or with alternative measurement/observation systems. FIGS. 9A, 10A and 11A provide partial perspective views of light directing assemblies 900, 1000, and 1100, and FIGS. 9B, 10B, 11B, and 12 provide partial elevation views of one optical relay assembly of the light directing assemblies 900, 1000, and 1100 respectively.

In each embodiment of FIGS. 9 to 12, the light directing assemblies 900, 1000, 1100, and 1200 direct light from a scanning mirror 112 to/into an object of interest 902 (which may be an eye-related system 106 or alternative object being observed/measured) at a plurality of interrogation angles. As with the previous embodiments, light directing assemblies 900, 1000, 1100, and 1200 each operate to provide for a predetermined optical path length relationship between the optical path lengths of the interrogation (and hence return) beams at each interrogation angle.

Figure 9B:
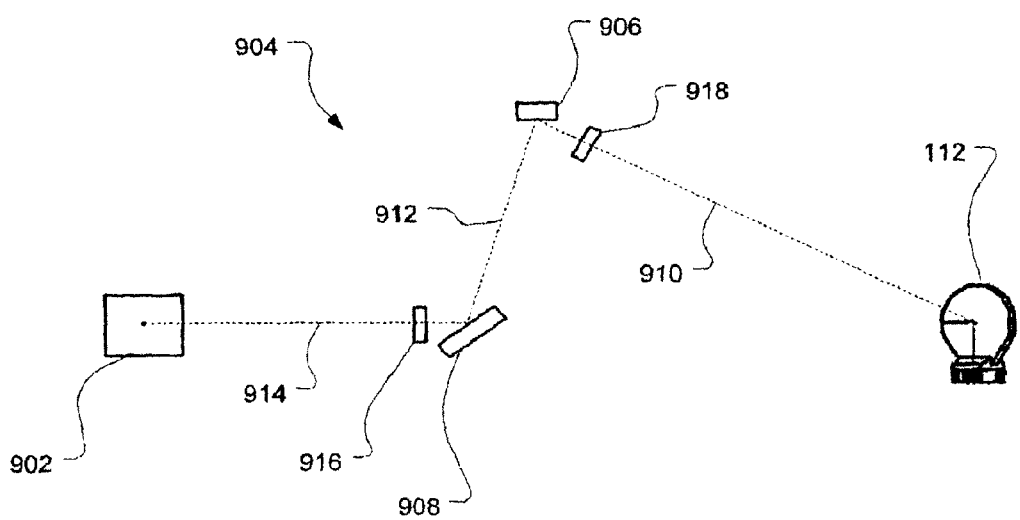
Figure 10A:
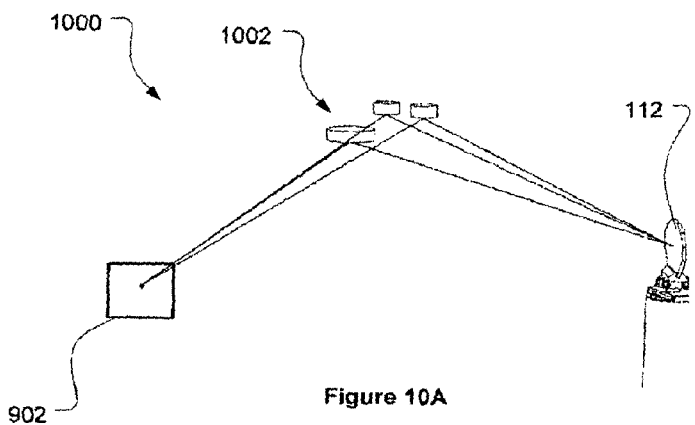
FIGS. 10A and 10B respectively provide partial perspective and elevation views of a light directing assembly in accordance with an alternative embodiment of the invention.

The light directing assembly 900 of FIG. 9 includes a plurality of optical relay assemblies 904 (only three of which are shown in FIG. 9A, and one in FIG. 9B). Each optical relay assembly 904 includes a central optical element 906 and an object-proximate element 908. Depending on the application and optical elements used, relay element 916 and 918 may also be used. To direct interrogation beams to (receive return beams from) the central optical elements 906, case scanning mirror 112 is movable about two axes (i.e. a horizontal axis and a vertical axis), allowing the scanning mirror 112 to pan and tilt. The central optical elements 906 direct interrogation/return beams between the scanning mirror 112 and the object-proximate elements 908, and the object-proximate elements 908 direct interrogation/return beams between the central elements 906 and the object 902. In this embodiment the optical paths 910 between the scanning mirror 112 and each central optical element 906 are not co-planar, but the optical paths 914 directed at/entering the object 902 (i.e. the between the object-proximate elements 908 and the object 902) are co-planar (defining a scan plane of the system).

By adjusting the position of the central element 906, the optical path length of a given optical relay assembly 904 in the light directing assembly 900 (i.e. the combination of optical paths 910, 912, and 914) can be set/controlled. Accordingly, by selective positioning of each of the central elements 906 of the optical relay assemblies 904, the desired predetermined optical path length relationship between the optical relay assemblies 904 can be set.

Figure 10B:
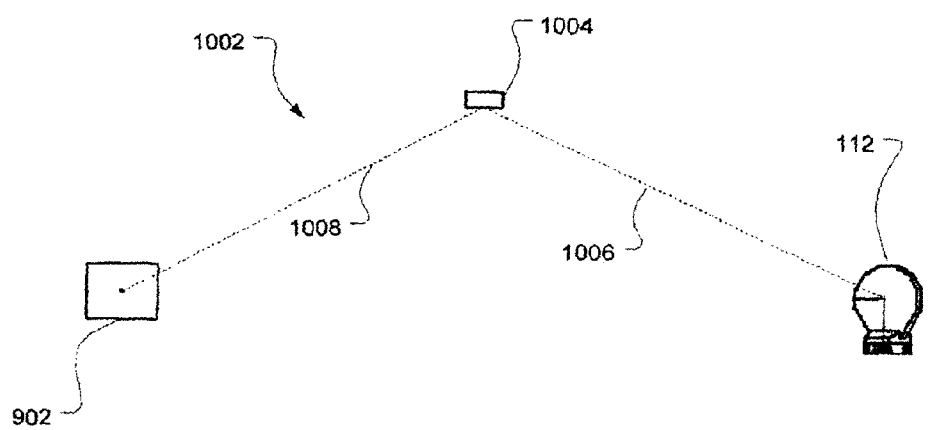
Figure 11A:
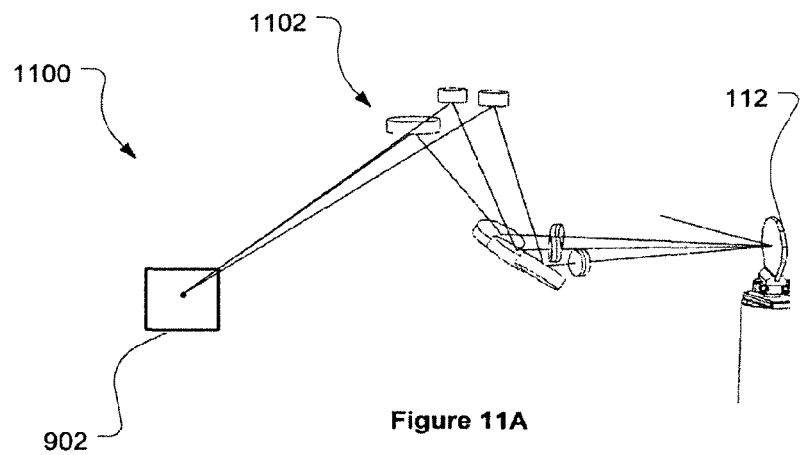
FIGS. 11A and 11B respectively provide partial perspective and elevation views of a light directing assembly in accordance with an alternative embodiment of the invention.

The light directing assembly 1000 of FIG. 10 includes a plurality of optical relay assemblies 1002 (only three of which are shown in FIG. 10A, and one in FIG. 10B). Each optical relay assembly 1002 includes a single central optical element 1004 positioned between the scanning mirror 112 and object being measured/observed 902. The central optical element 1004 directs interrogating beams directly from the scanning mirror 112 to the object 902, and return beams from the object 902 back to the scanning mirror 112. Typically, relay elements (not shown) will be positioned between the scanning mirror 112 and the central optical element 1004, and between the central optical element 1004 and the object 902. As with the embodiment of FIG. 9, scanning mirror 112 is movable about two axes to pan and tilt to directly transmit interrogation beams to (and receive return beams from) the central optical elements 1004 of the light relay assemblies 1002.

The embodiment of FIG. 10 may be arranged/configured such that the scanning plane is planar (i.e. the optical paths 1006 between the scanning mirror 112 and each central optical element 1006 are co-planar). Alternatively, the embodiment of FIG. 10 may be arranged/configured such that the scanning plane is not planar (i.e. the optical paths 1006 between the scanning mirror 112 and each central optical element 1006 are not co-planar), nor are the optical paths 1008 between the object 902 and each of the central elements 1004. In this case, though, the light directing assembly could be configured such that the deviation from a common scan plane was relatively small, still allowing for useful data to be obtained (e.g. refraction data from an eye-related system). Further, if the light directing assembly 1000 is rotated around its optical axis to obtain a full 3D peripheral refraction map, the measured points could be interpolated to achieve a continuous map.

By adjusting the position of the central element 1004, the optical path length of a given optical relay assembly 1002 in the light directing assembly 1000 (i.e. the combination of optical paths 1006 and 1008) can be set/controlled. Accordingly, by selective positioning of each of the central elements 1004 of the optical relay assemblies 1002, the desired predetermined optical path length relationship between the optical relay assemblies 1002 can be set.

Figure 11B:
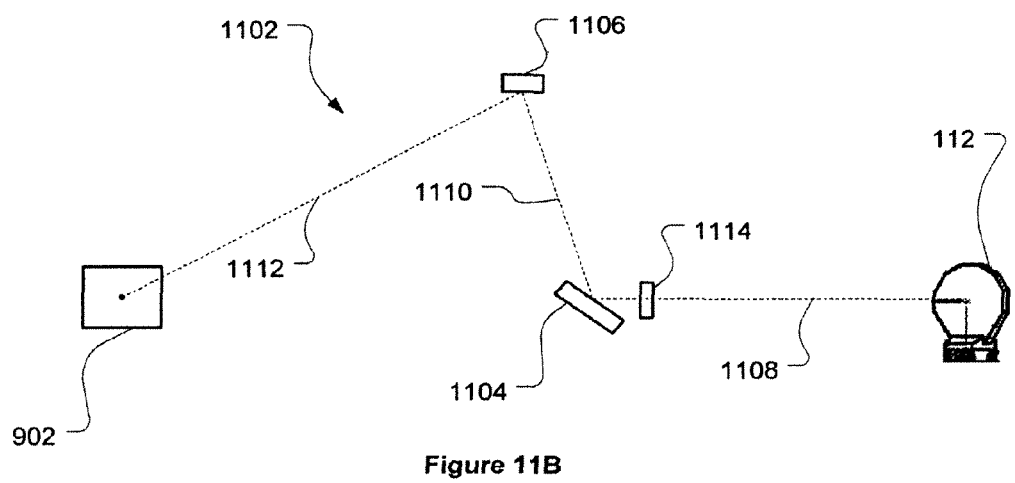

The light directing assembly 1100 of FIG. 11 includes a plurality of optical relay assemblies 1102 (only three of which are shown in FIG. 11A, and one in FIG. 11B). Each optical relay assembly 1102 includes a source-proximate optical element 1104, a central element 1106, and relay elements 1114. Typically, an additional relay element (not shown) will be positioned between the object 902 and the central element 1106. In this embodiment the source-proximate elements 1104 are illuminable by co-planar beams (as with the embodiment of FIG. 1), and as such scanning mirror 112 need only be movable about a single axis in order to pan between the source-proximate elements 1104 of the optical relay assemblies 1102. The source-proximate elements 1104 direct interrogation/return beams between the scanning mirror 112 and the central elements 1106, and the central elements 1106 direct interrogation/return beams directly to/from the object 902. As with the light directing assembly 1000 of FIG. 10, the light directing assembly 1100 of the present embodiment may be arranged/configured such that the optical paths 1112 between the object 902 and each central optical element 1106 are either planar or not co-planar. Optical paths 1108 between the source proximate elements 1104 and the scanning mirror 112 are co-planar on a transmission plane.

By adjusting the position of the central element 1106, the optical path length of a given optical relay assembly 1102 in the light directing assembly 1100 (i.e. the combination of optical paths 1108, 1110, and 1112) can be set/controlled. Accordingly, by selective positioning of each of the central elements 1106 of the optical relay assemblies 1102, the desired predetermined optical path length relationship between the optical relay assemblies 1102 can be set.

Figure 12:
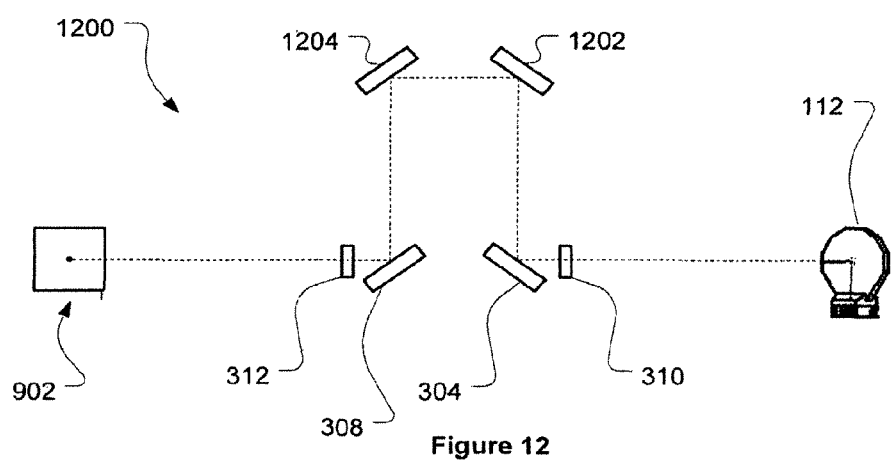
FIG. 12 provides a partial elevation view of a light directing assembly in accordance with a further alternative embodiment of the invention.

In the embodiment of FIG. 12, instead of a single central element one or more of the optical relay assemblies 116 is provided with two central optical elements 1202 and 1204. In this case the first central element 1202 directs light between the source-proximate element 304 and the second central element 1204, and the second central element 1204 directs light between the eye-related system-proximate element 308 and the first central element 1202). By employing two central optical elements in an optical relay assembly, the optical path lengths of all the optical relays can be adjusted in synchrony (e.g. by use of an actuator) by moving the two central optical elements in unison. Alternatively, the optical elements of the relay assemblies may be individually adjusted to provide a different path length relationship between the optical relay assemblies.

Figure 13A:
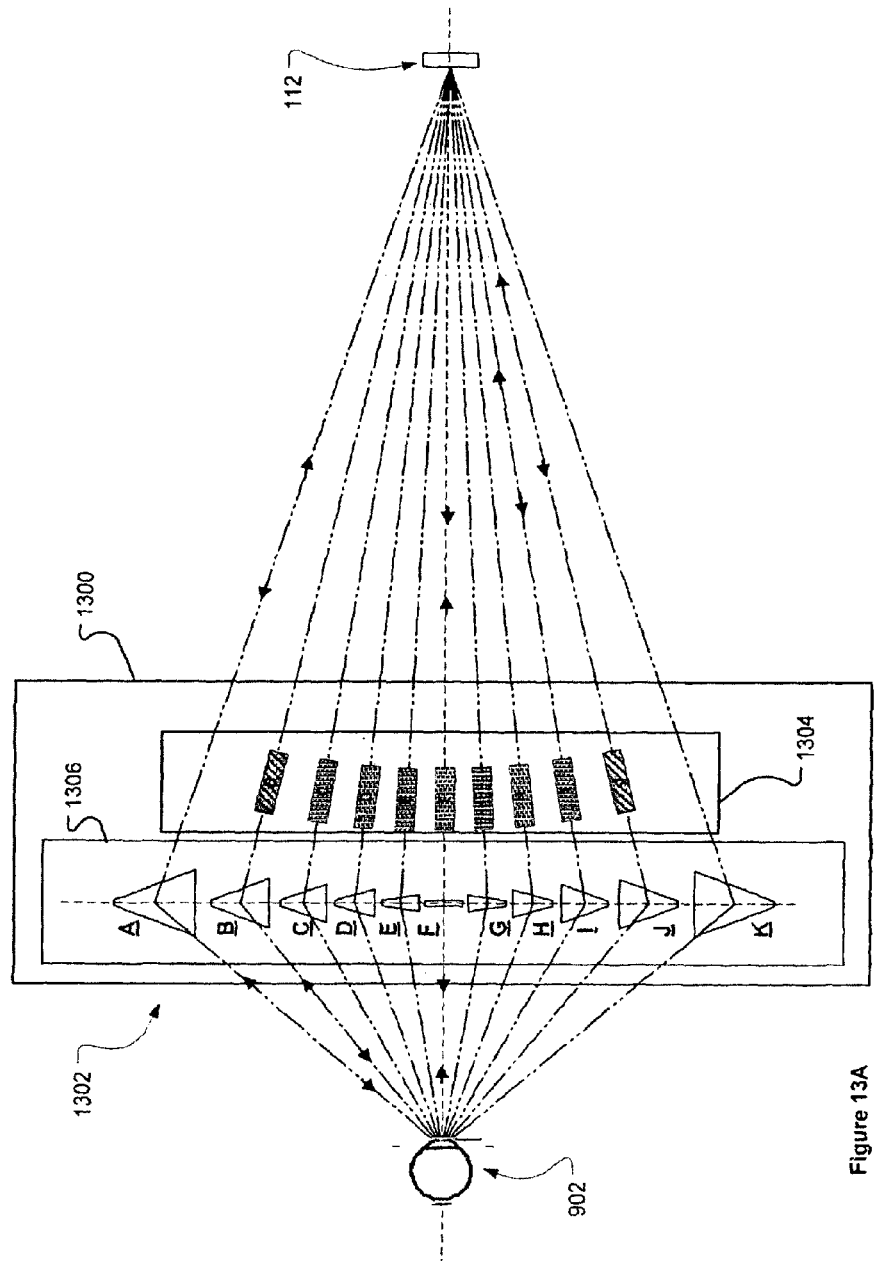

The light directing assembly 1300 of FIGS. 13A and 13B is a modification of an assembly described in patent publication number WO 2008/116270 A1 (application number PCT/AU2008/000434), published on 2 Oct. 2008 and titled "Characterising eye-related optical systems", which is hereby incorporated in its entirety by reference.

Each optical relay assembly 1302A to 1302K in assembly 1300 includes a light directing element 1306A to K (as described in WO 2008/116270). In addition, however, each optical relay assembly 1302B to 1302J includes a path length adjustment means, which in the embodiments of FIGS. 13A and 13B is an adjustment element 1304B to 1304J. Adjustment elements 1304 are provided to adjust the optical path length of the optical relay assemblies, thereby providing the predetermined optical path length relationship between the optical paths of each relay assembly 1302 (e.g. such that the optical path lengths are equal). Light directing elements 1306 may be prisms or similar, and serve to direct interrogation/return beams between the object of interest 902 (e.g. an eye-related system) and the scanning mirror 112 (via the adjustment elements as appropriate).

Adjustment elements 1304 in the present case are parallel sided optical glass elements with a refractive index of greater than 1. As will be appreciated, optical path elongation by these elements may be achieved in a variety of ways. For example, in FIG. 13A the adjustment element 1304 for a given relay assembly 1302 has a refractive index selected so as to provide for the desired path elongation. Alternatively, in FIG. 13B the adjustment element 1304 for a given optical relay assembly 1302 has a size (e.g. length or width) selected in order to provide the desired path elongation.

In FIGS. 13A and 13B, the light directing element 1306 and path length adjustment means 1304 have been depicted as separate optical components. In further alternative embodiments, however, a single optical component (e.g. an elongated prism type element) may be used to achieve both the light direction functionality of elements 1306 and the path elongation functionality of elements 1304.

FIG. 13C provides an elevation depiction of an alternative path length adjustment means 1310 suitable for use with light directing assemblies 1300 (or, indeed, light directing assemblies of any of the preceding embodiments). Path length adjustment means 1310 (or a variation thereof) may be used in addition to or instead of adjustment elements 1304 to adjust the optical path length of a given relay assembly. Adjustment means 1310 is a path length adjustment assembly which includes a pair of optical elements 1312 and 1314 (in this instance parallel sided glass plates) which are angled so as to deflect the interrogation/return beam 1316 out of and back into the original beam axis (indicated by dotted line 1318). Different optical path lengths may be provided by adjustment means 1310 according to the thickness of the optical elements 1312 and 1314, the refractive indices of the optical elements 1312 and 1314, the angle at which elements 1312 and 1314 are placed in the optical path (with a more perpendicular angle providing for less deflection and path elongation), or a combination of thickness, refractive index, and angle.

A light directing assembly may, of course, utilise a combination of different types of path length adjustment means. For example, some optical relay assemblies may provide the desired path elongation via adjustment elements of particular refractive indices, by adjustment elements of particular widths, by adjustment means such as means 1310, and/or by adjustment means using various combinations thereof. Such adjustment means may also be used in the light directing assemblies of the foregoing embodiments.

As will be appreciated, the central optical relay assembly 1302F provides for the shortest geometrical path length, with increased scanning angles providing progressively longer geometrical path lengths (with the longest geometrical path lengths being at the largest/peripheral scanning angles—1302A and 1302K). As the path length provided by the peripheral optical relay assemblies 1302A and 1302K is the longest path of the system, adjustment elements may not be necessary for these optical relay assemblies (with adjustment elements 1304B to 1304J all being selected to provide a path length that is equal (or otherwise related) to the path length of relay assemblies 1302A and 1302K.

In alternative embodiments, however (e.g. where it is necessary or advantageous for a predefined path length relationship that requires a longer path length than is "naturally" provided by relay assemblies 1302A and 1302K), relay assemblies 1302A and 1302K may, of course, also be provided with adjustment elements to elongate their optical path lengths.

Light directing assemblies of FIGS. 13A and 13B may provide an advantage in certain applications by providing an assembly in which the optical elements are all be positioned in a single plane.

Further alternative embodiments of the light directing assembly of the invention may provide multiple, non coplanar optical paths to provide for scan planes (i.e. measurement axes) in multiple angular dimensions. For example, an assembly may be configured to provide measurement axes in two angular dimensions: a first angular dimension as per the embodiments described above, and a second optical interrogation/receive axis (as seen by the scanning mirror) provided by a second set of optical elements positioned on a measurement plane parallel to, but above or below the main scan (and measurement) plane. In this instance an optical element (e.g. element 306/906) would be operated to selectively direct interrogation/return beams both between the "horizontal" interrogation angles (as per the previously described embodiments) and the "vertical" interrogation angles to provide, for example, a set of measurements such as: (vert 0 deg)[+40, +20, 0, −20, −40] and (vert 20 deg)[+40, +20, 0, −20, −40]. (Other vertical/horizontal angles also being possible.)

This example could, of course, be extended to include a third (and further) set of optical elements positioned in a third measurement plane located above or below the main scan plane. Each third axis as seen by the scan mirror would map to each third measurement plane.

While, in some applications/embodiments, features/components of the light directing assemblies and measurement/observations systems are advantageous, it will be understood that not all features/components are strictly necessary in all applications/embodiments.

It will also be understood that the invention disclosed and defined in this specification extends to all, alternative combinations of two or more of the individual features mentioned or evident from the text or drawings. All of these different combinations constitute various alternative aspects of the invention.

The invention claimed is:

1. A light directing assembly for use in an eye analysis system, the light directing assembly comprising:
a plurality of optical relay assemblies, each optical relay assembly including at least one optical element configured to:
relay an interrogation beam from a light transmission system to an eye; and
relay a return beam from the eye to the light transmission system, the return beam being generated by reflection or back scattering of the interrogation beam by the eye,
wherein each optical relay assembly defines:
an interrogation angle at which the interrogation beam relayed by the optical relay assembly reaches the eye, and
an optical path length being the distance from the light transmission system to the eye traveled by an interrogation beam via the optical relay assembly,
wherein the range of interrogation angles, as defined relative to the optical axis of said eye, is at least ten degrees, and
wherein the plurality of optical relay assemblies are further configured such that the optical path length for a given optical relay assembly has a predefined relationship with the optical path lengths of the other optical relay assemblies.

2. A light directing assembly according to claim 1, where the optical path lengths of the optical relay assemblies are independently adjustable.

3. A light directing assembly according to claim 1, wherein the predefined relationship between the optical path lengths is that the optical path lengths of all optical relay assemblies are substantially equal.

4. A light directing assembly according to claim 1, wherein each optical relay assembly includes a plurality of optical elements, the plurality of optical elements of each optical relay assembly including a central optical element for directing the interrogation beam towards the eye and for directing the return beam towards the light transmission system.

5. A light directing assembly according to claim 4, wherein each optical relay assembly further includes a light transmission system-proximate optical element, the light transmission system-proximate optical elements of the plurality of optical relay assemblies arranged to receive interrogation beams from the light transmission source on a common transmission plane.

6. A light directing assembly according to claim 5, wherein the transmission plane is co-planar with the scan plane.

7. A light directing assembly according to claim 1, wherein each optical relay assembly includes an eye-proximate optical element, the eye-proximate optical elements of the plurality of optical relay assemblies arranged to relay interrogation beams to the eye on a common scan plane.

8. A light directing assembly according to claim 7, wherein the light directing assembly is rotatable by a rotation means to adjust the common scan plane on which the interrogation beams from the eye-proximate optical elements are relayed to the eye.

9. A light directing assembly according to claim 7, wherein each central optical element is positioned in a plane normal to the scan plane.

10. A light directing assembly according to claim 7, wherein at least one central optical element is movable by an actuator in a plane normal to the scan plane, movement of the central optical element changing the optical path length defined by that light relay assembly.

11. A light directing assembly according to claim 1, wherein the light transmission system is a scanning mirror.

12. A light directing assembly according to claim 1, wherein the scanning mirror is movable in two dimensions.

13. A light directing assembly according to claim 1, wherein each of a plurality of the optical relay assemblies further includes a path length adjustment means for adjusting the optical path length of the optical relay assembly.

14. A light directing assembly according to claim 13, wherein the path length adjustment means for a given optical relay assembly includes an adjustment element having a refractive index selected to provide that optical relay assembly with an optical path length which accords with the predefined optical path length relationship.

15. A light directing assembly according to claim 13, wherein the path length adjustment means for a given optical relay assembly includes an adjustment element having a size selected to provide that optical relay assembly with an optical path length which accords with the predefined optical path length relationship.

16. A light directing assembly according claim 13, wherein the path length adjustment means for a given optical relay assembly includes a pair of optical elements configured to adjust the path length of the optical relay assembly by deflecting the interrogation and return beams out of and back into an original beam axis.

17. An object analysis system for optically analysing an object, the object analysis system including:
a light directing assembly according to claim 1;
a light source adapted to generate and propagate a source light beam along a source beam path to a light transmission system, the light transmission system optically connected to said source beam path and adapted to generate and direct interrogation beams at each optical relay assembly in the light directing assembly, the light transmission system further adapted to receive return beams from the optical relay assemblies and direct said return beams along said source beam path;
a detector for detecting each return beam and generating a detector output data indicative of each detected return beam, and
a processing system in communication with said detector, said processor adapted to:
receive said detector output data;
compare data relating to each detected return beam with data representative of the interrogation beam that generated that return beam; and
generate an analysis output indicating aberrations between pairs of return beam data and corresponding interrogation beam data.

18. An object analysis system according to claim 17, further including a first beam splitter located in said source beam path and adapted to divert a least portion of each return beam directed along said source path to said detector.

19. An object analysis system according to claim 17, wherein the light transmission system includes a beam scanner adapted to scan said source light beam over the optical relay assemblies so as to generate a succession of interrogation beams and return beams.

20. An object analysis system according to claim 17, further including an encoding means adapted to differentially encode a plurality of return beams to facilitate separate detection thereof by said detector means.

21. An object analysis system according to claim 17, wherein the object a human eye or a model thereof, the eye having a cornea surface and a retina surface such that each return beam has a first component indicative of reflection from the cornea and a second component indicative of reflection from the retina, wherein:
the object analysis system has an interferometer beam path that intersects said source beam path,
a second beam splitter located in the intersection of said source path and said interferometer beam path and adapted to divert portion of the source beam into said interferometer beam path as a reference beam and to divert portion of a return beam travelling in said source beam path into said interferometer beam path,
an interference detector arranged at one end of said interferometer beam path and is connected to said processor so as to signal the processor when an interference between said reference beam and said return beam in said source path is detected,
a reflector arranged at the other end of said interferometer beam path,
a reflector actuator connected to said reflector and to said processing system for reciprocating the reflector along said interferometer beam path under the control of the processing system so as to change the effective length of said interferometer beam path, and
during operation, interference between said first component of the return beam and the reference beam is signalled to the processing system together with a first position of the reflector actuator, and interference between said second component of the return beam and the reference beam is signalled to the processing system together with a second position of the reflector actuator, to thereby enable said processing system to compute the distance between the cornea and the retina of the eye along the path of the return beam within the eye.

22. A light directing assembly according to claim 21, wherein the relay lenses are equidistant from the light transmission system.

23. A light directing assembly according to claim 1, further comprising relay lenses that capture and refocus at least one of the beams.

24. A light directing assembly according to claim 1, further comprising a non-spherical concave mirror.

25. A light directing assembly according to claim 1, wherein the predefined relationship between the optical path lengths is that the optical path lengths of all optical relay assemblies are not substantially equal.

26. A light directing assembly according to claim 1, further comprising a photo detector.

27. A light directing assembly according to claim 1, further comprising a wavefront sensor.

28. A light directing assembly according to claim 1, wherein the range of interrogation angles is at least from −10° to +10°.

29. A light directing assembly according to claim 1, wherein the range of interrogation angles is at least from 10° to 40°.

* * * * *